US006824309B2

(12) United States Patent
Robert-Coutant et al.

(10) Patent No.: US 6,824,309 B2
(45) Date of Patent: Nov. 30, 2004

(54) DOUBLE ENERGY RADIOGRAPHY METHOD, AND CALIBRATION DEVICE FOR THIS METHOD

(75) Inventors: Christine Robert-Coutant, St Martin d'Uriage (FR); Jean-Marc Dinten, Lyons (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/731,670

(22) Filed: Dec. 9, 2003

(65) Prior Publication Data

US 2004/0119007 A1 Jun. 24, 2004

Related U.S. Application Data

(63) Continuation of application No. 10/075,209, filed on Feb. 14, 2002, now abandoned.

(30) Foreign Application Priority Data

Feb. 16, 2001 (FR) .............................................. 01 02140

(51) Int. Cl.$^7$ ............................................. G01D 18/00
(52) U.S. Cl. ...................................................... 378/207
(58) Field of Search ........................................... 378/207

(56) References Cited

U.S. PATENT DOCUMENTS

5,095,499 A   3/1992   Wentz
6,231,231 B1  5/2001   Farrokhnia et al.
6,315,447 B1  11/2001  Nord et al.

FOREIGN PATENT DOCUMENTS

EP   1 062 912 A1   12/2000
EP   1 072 223 A1   1/2001

*Primary Examiner*—Craig E. Church
(74) *Attorney, Agent, or Firm*—Pearne & Gordon LLP

(57) ABSTRACT

In a radiography method with double energy conical beam, a preliminary calibration of the system involves using a device made up of blocks of different thicknesses of a first material, in stepped form here (1), composed of layers (2, 3, 4, 5), and which further comprises inserts (7) partly formed (12) of another material. A sufficient number of thickness combinations crossed by the radiation is obtained for each of the materials, while still producing scattered radiation resembling that of the subject, because of the similarity of the proportions and distribution of the two materials; a single digital method for estimation and correction for scattered radiation can then be applied.

4 Claims, 2 Drawing Sheets

DOUBLE ENERGY RADIOGRAPHY METHOD, AND CALIBRATION DEVICE FOR THIS METHOD

This application is a continuation of application Ser. No. 10/075,209 filed on Feb. 14, 2002 now abandoned.

The present invention relates to a double energy radiography method, together with an appropriate calibration device for this method.

Double energy radiography consists of exposing an subject or a patient to radiation with two different energies, for which the attenuation properties of the materials constituting the subject or the patient do not vary in the same way. Using a model of their attenuation functions, one thus obtains information about the density and nature of the material crossed through. In particular, in the case of bone densitometry, the bone mass crossed can be calculated by distinguishing it from the contribution of soft tissues to attenuation of the radiation.

The theoretical basis of the method will be resumed briefly below.

The flux $\phi$, after crossing a length l of a material with linear attenuation coefficient $\mu$ from an initial radiation flux $\phi_0$, is equal to $\phi = \phi_0 e^{-\mu l}$. The attenuation measurement is named m, equal to $$\ln\left(\frac{I_0}{I}\right)$$

where $I_0$ and $I$ are signals measured by a same detector under the fluxes $\phi_0$ and $\phi$. In the case of a complex subject composed of a large number of materials (of index i), each one contributes to attenuation according to its length $L_i$ crossed by the rays.

However, each material can be expressed, for its attenuation property, as a linear combination of two base materials, according to the formula:

$$\mu = k_1 \mu_1 + k_2 \mu_2,$$

where $k_1$ and $k_2$ are constant coefficients, and $\mu_1$ and $\mu_2$ represent the attenuation of these base materials, and the equivalent lengths $A_1$ and $A_2$ of the base materials crossed by the radiation by:

$$\begin{cases} A_1 = \sum_i L_i \cdot k_1 \\ A_2 = \sum_i L_i \cdot k_2 \end{cases}$$

By means of these equivalent lengths, the base materials can represent a subject even if in reality its composition is much more complex. Even if the materials composing the subject are different from the base materials, the breakdown has a meaning. In the case of examining living beings, the classic base materials are Plexiglas (polymethacrylate) to simulate soft tissues and hydroxyapatite to simulate bone tissues.

The system of equations linking the measurements to the attenuation $\mu_1$ and to the equivalent lengths $A_j$ of the base materials is linear and therefore simple to solve if the radiation is monochromatic. But this is not so for real situations, and the equivalent lengths are then given by more complicated mathematical models, such as:

$$\begin{cases} A_1 = a_0 + a_1 \cdot mBE + a_2 \cdot mHE + a_3 \cdot mBE \cdot mHE + a_4 \cdot m_{BE}^2 + a_5 \cdot m_{HE}^2 \\ A_2 = b_0 + b_1 \cdot mBE + b_2 \cdot mHE + b_3 \cdot mBE \cdot mHE + b_4 \cdot m_{BE}^2 + b_5 \cdot m_{HE}^2 \end{cases}$$

which generally provide sufficient precision, and where mBE and mHE represent the attenuation measurements at high and low energy, and "a" and "b" are coefficients which must be calculated beforehand by calibration.

This calibration requires a device which is often called a "phantom" and which is composed of base materials as described above and chosen in order to simulate the subject to be measured as closely as possible. These materials are distributed in the phantom in such a way as to provide regions where the lengths of materials, crossed by the radiation, are distributed differently.

A classic phantom is built up in the form of a staircase for each of the measuring materials, and the stairs are superposed in such a way that their steps are perpendicular. By making vertical rays cross the steps, one thus obtains all the required combinations between the diverse thicknesses of the two materials.

Another phantom is proposed in the U.S. Pat. No. 5,493,601 and comprises a series of tubes converging towards the source of the beam and provided with heights divided unequally between the two materials. The aim is to provide more exact measurements than previously, in particular because of the convergence of the tubes towards the source, which makes the length the rays pass through in the tubes coincide perfectly with the total height of the latter, and also reduces the scattered radiation by containment in the tubes. The measurements are thus a direct expression of the attenuation of the radiation through the phantom and make it possible to calculate the coefficients required reliably.

However, the same cannot be said for the measurements produced through the subject to undergo radiography, for which the favourable conditions described above cannot be assembled and the scattered radiation must not be neglected; it is even especially important for sources with a conical beam, often more so than for the primary radiation, which has followed a straight line trajectory from the source to the detector and is the only one useful for the measurement. The estimation and then correction of this scattered radiation requires specific processing. Thus, amongst other methods, it is possible to measure it separately and then to subtract it from the total radiation received by the detector. In order to do this, one uses a network of absorbent elements, such as lead balls arranged in such a way as to form a grid. The balls are glued on Plexiglas and set in a homogeneous pattern, regular, for example, for the lines and columns so as to allow interpolation between the balls, between the radiographed subject and the detector's network of pixels. The rays intended to pass through these balls are intercepted totally, so that only the scattered radiation reaches the pixels of the detector located in the path of these rays. Digital interpolations then make it possible to estimate, with sufficient precision, the distribution of the scattered radiation over the whole of the detector's pixels. This convenient method, however, has the disadvantage of having to submit the subject to a second irradiation, which may be difficult for living beings to accept.

On the other hand, one can also prevent the scattered radiation from reaching the detectors by providing them with a strict collimation for interception. The methods using this technique necessitate the use of source scanning which implies a long acquisition time and the risk that the subject may move during measurement.

Digital methods of various types have also been proposed to correct the influence of scattered radiation, but generally they are only suitable for particular subjects. It has to be concluded that the patent quoted above does not appear to propose any notable progress, since the scattered radiation is only separated from the measurements at the calibration stage.

The aim of the present invention is to correct the influence of the scattered radiation in another way, by allowing it to appear during calibration, but in an analogous manner to its behaviour during radiography of the subject, which makes it possible to correct it by an identical digital method, without fear of discordance of quality for this method.

To resume, the invention concerns above all a calibration device for a double energy radiography system, comprising a range of blocks with different thicknesses of a first material, characterised in that the blocks are provided with recesses and in that furthermore the device comprises inserts to fill up the recesses and including different distributions of heights, the heights and the thicknesses being considered in an identical direction, between the first material and a second material; together with a radiography method with a double energy conical beam, comprising a thickness estimation of materials of a radiographic subject by a digital combination of measurements of attenuation of energies, involving a coefficient calibration of the combination, characterised in that the calibration is measured by a radiography of a calibration device conforming to any one of the preceding claims, and that scattered radiation affecting the radiography of the calibration device is estimated while providing an estimation criterion used afterwards to estimate a scattered radiation affecting the radiography of the subject.

The invention will now be described with reference to the figures.

Figure 1:
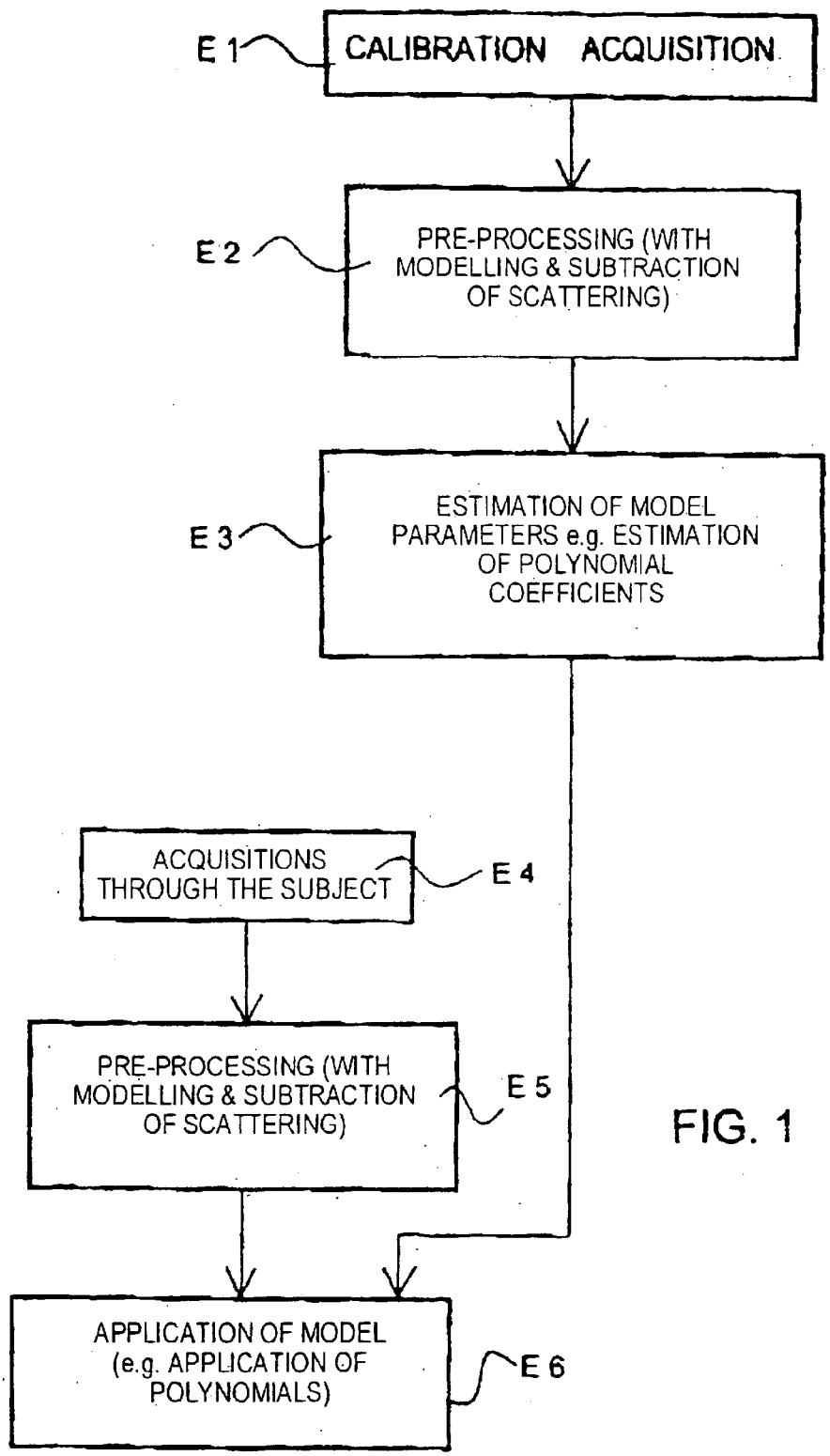
FIG. 1 shows a flow chart of the invention.

Reference is now made to FIG. 1.

At stage E1, a calibration acquisition is carried out by a radiography through the phantom described below, which gives rough measurements at high and low energy. At stage E2, preliminary processing for estimating and subtracting the scattered radiation from these measurements is made in order to calculate the corrected measurements mHe and mBe of the above formulae. Next, stage E3 consists of an estimation of the parameters of the model, particularly the polynomial coefficients a and b, from measurements and the known thicknesses the radiation crosses in the phantom. Furthermore, an acquisition, through the measured subject, is carried out at stage E4, then a preliminary processing is made at stage E5; it is similar to that of stage E2 and its aim is also to estimate and then subtract the scattered radiation which affects the measurements. The final stage E6 consists of using the corrected measurements made through the subject and applying the model, and above all the coefficients a and b calculated at stage E3, in order to deduce the equivalent lengths of the base materials a1 and a2 in the subject.

Figure 2:
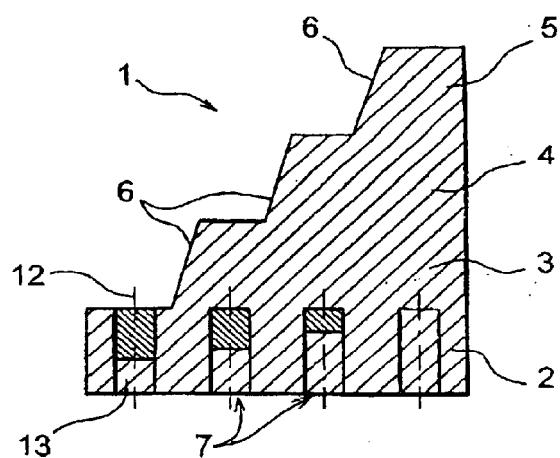
FIGS. 2 and 3 show views from the side and from above of a calibration phantom used to satisfy the requirements described above.
Figure 3:
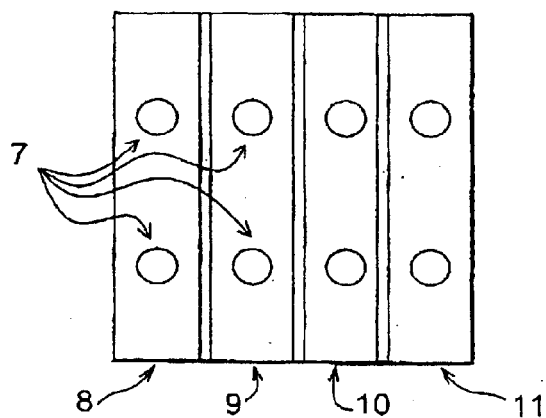

An example of a phantom is shown in FIGS. 2 and 3.

Figure 2A:
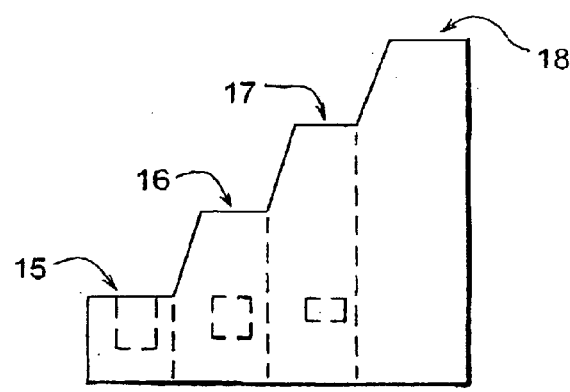
FIG. 2A identifying the blocks.

It comprises several blocks 15, 16, 17 and 18 (FIG. 2A) of different thicknesses of one of the base materials, in particular, Plexiglas. An assembly (not shown) of separate blocks could be used, through which the measurements would be made successively, but the blocks 15, 16, 17 and 18 can be parts of a united solid 1 too, which has a stepped profile and may be comprised of different layers usually finishing by dressed tapered faces 6, so as to reduce the high frequency components of the scattered radiation. Furthermore, rows of inserts are provided under the different blocks, filling the recesses made here through the lower layer 2. More precisely, one finds four rows of two inserts 7 for each, numbered 8 to 11, which extend respectively under the upper surface of the lower layer 2, under the second layer 3, under the layers 3 and 4 and under the three upper layers 3 to 5. Generally, the inserts 7 comprise a portion in hydroxyapatite 12 and a portion in Plexiglas 13. The portions 12 and 13 have the same total height, but different respective heights in each row 8 to 11, such that the rays originating from the source 14 and which pass through each of the inserts 7, cross different combinations of thicknesses of the two materials. Furthermore, scattered radiation is produced analogous to that produced in a living being. This similitude is due to the constitution of phantom 1 itself since the materials composing it, apart from simulating closely the soft tissues and the bones, have analogous proportions and distributions. In particular, the inserts 7 are sufficiently separated so that they do not receive scattered radiation coming from neighboring inserts, but only from the base material of layers 2 to 5.

Finally, this description will detail a method for estimation of scattered radiation, applicable for use in stages E2 and E5; however this method is part of another invention and is therefore only given in order to complete the description of this one and to prove the interest of the phantom 1.

At the stage E2, radiation similar to that to be used on the subject and with flux $\varnothing_0$ is directed at the phantom 1, and a total radiation $\varnothing_t$, the sum of a primary radiation $\varnothing$ and the scattered radiation $\varnothing_d$, is collected by the detectors placed behind the phantom 1, thus measuring the attenuation through it of the initial radiation $\varnothing_0$. In particular, one obtains measurements of radiation after passing across each of the inserts 7, both for high and low energy.

The same measurements are repeated after setting absorbers in place, such as lead balls, between the source and the phantom in such a way as to intercept the primary radiation and only to measure the scattered radiation by the detectors behind the lead balls. By interpolation one then deduces the value of the diffused radiation $\varnothing_d$ in function of the heights of the two base materials crossed for each of the energies.

The acquisition of the measurements through the subject also provides two ranges of values for total radiation $\varnothing_t$ at high and low energy. The radiation $\varnothing_d$ through the subject can be estimated according to the measurements behind the lead balls through the phantom 1 and the relation between $\varnothing_t$, $\varnothing_d$ and $\varnothing$ obtained through it for the two energies, assuming that the same relation applies through the subject.

Although the invention is useful for conical beams, its use is not limited to these; one can conceive the stages of estimation and correction of scattered radiation being omitted in situations where it would be of less importance, since it would affect the measurements through the phantom 1 and the subject similarly, because of their similarity of structure, and its influence would disappear for the calculation of equivalent lengths $A_1$ and $A_2$.

What is claimed is:

1. Device (1) for calibrating a system for double energy conical beam radiography, comprising an assembly of blocks of different thicknesses of a first material, characterized in that the blocks are provided with recesses and in that the device further comprises inserts (7) of a second material to fill the recesses and comprising different height distributions (12, 13), the heights of the inserts and the thicknesses of the blocks being considered in an identical direction, the first material and the second material simulating respective first and second material of an object to be examined by the system, the inserts having proportions and distributions in the blocks which are analogous to proportions and distributions of the second material of the object in the first material of the object.

2. Calibration device according to claim 1, characterized in that the blocks are assembled in stepped form and the inserts are divided into rows (8 to 11) in a lower layer (2) of the steps, the, rows being located under different blocks.

3. Calibration device according to claim 2, characterized in the steps have tapered faces (6).

4. Method for radiography of an object with a double energy conical beam, comprising an estimation of thicknesses of materials of the object by a digital combination of measurements of energy attenuation, involving calibration of coefficients of the combination, wherein the calibration is made with an assembly of blocks of different thicknesses of a first material, the blocks being provided with recesses and further comprising inserts (7) of a second material to fill the recesses, the inserts comprising different heights (12, 13), the heights of the inserts and the thicknesses of the blocks being considered in an identical direction, the first material and the second material simulating respective first and second materials of the object, the inserts having proportions and distributions in the blocks which are analogous to proportions and distributions of the second material of the object in the first material of the object, the device being designed so that the inserts are sufficiently separated to not receive scattered radiation coming from neighboring inserts, wherein a total radiation and a scattered radiation through the device are measured successively, a relationship between the total radiation and the scattered radiation is established, and the energy attenuation measured through the object is further estimated with said relationship for correcting the scattered radiation through the object, before the combination of the measurement is made.

* * * * *